(12) United States Patent
Isik

(10) Patent No.: US 11,523,958 B2
(45) Date of Patent: Dec. 13, 2022

(54) DEVICE FOR THE DISCHARGE OF URINE

(71) Applicant: Hasan Hueseyin Isik, Wil SG (CH)

(72) Inventor: Hasan Hueseyin Isik, Wil SG (CH)

( * ) Notice: Subject to any disclaimer, the term of this patent is extended or adjusted under 35 U.S.C. 154(b) by 0 days.

(21) Appl. No.: 17/046,112

(22) PCT Filed: Apr. 11, 2019

(86) PCT No.: PCT/CH2019/000012
§ 371 (c)(1),
(2) Date: Oct. 13, 2020

(87) PCT Pub. No.: WO2019/195950
PCT Pub. Date: Oct. 17, 2019

(65) Prior Publication Data
US 2021/0038457 A1 Feb. 11, 2021

(30) Foreign Application Priority Data

Apr. 12, 2018 (CH) .................................. 00466/18

(51) Int. Cl.
*A61G 9/00* (2006.01)
*A61F 5/48* (2006.01)
*A61G 7/02* (2006.01)

(52) U.S. Cl.
CPC ................ *A61G 9/006* (2013.01); *A61F 5/48* (2013.01); *A61G 7/02* (2013.01)

(58) Field of Classification Search
CPC ........... A61G 7/02; A61G 9/003; A61G 9/006
See application file for complete search history.

(56) References Cited

U.S. PATENT DOCUMENTS

| 183,973 A | 10/1876 | Rhodes |
| 1,779,742 A | 10/1930 | Lines |
| 2,384,325 A | 9/1945 | Marsan |
| 2,654,898 A * | 10/1953 | Eckart ...................... A61G 7/02 5/695 |
| 2,971,204 A | 2/1961 | McCoy et al. |
| 3,329,104 A | 7/1967 | Gittings |
| 3,345,652 A | 10/1967 | Hiraga |

(Continued)

FOREIGN PATENT DOCUMENTS

| CA | 2394796 A1 | 5/2001 |
| CH | 714896 A2 | 10/2019 |

(Continued)

OTHER PUBLICATIONS

ISR and written opinion, dated May 29, 2019, from parent International appl. PCT/CH2019/000012 published as WO2019/195950A1, with English translation of ISR.

(Continued)

*Primary Examiner* — Robert G Santos
*Assistant Examiner* — Adam C Ortiz

(57) ABSTRACT

Devices for the discharge of bodily waste, in particular for the soiling-free discharge of bodily waste from a person situated on a bed or a seat. A bed's mattress (2) is provided with a slot (4) that may be opened and closed, and which extends continuously through the thickness of the mattress (2). The slot is controllably openable and closable via an actuated mechanism. Hygienic elimination of bodily waste while lying down or sitting may be achieved with little effort.

14 Claims, 1 Drawing Sheet

(56) References Cited

U.S. PATENT DOCUMENTS

| | | | |
|---|---|---|---|
| 3,922,735 A | 12/1975 | Kato | |
| 5,737,786 A | 4/1998 | Yamamoto | |
| 6,651,267 B1 | 11/2003 | Utz | |

FOREIGN PATENT DOCUMENTS

| | | | | |
|---|---|---|---|---|
| DE | 19916283 A1 | | 10/2000 | |
| DE | 10103910 B4 | | 9/2004 | |
| FR | 2724841 A1 | * | 3/1996 | ............... A61G 7/02 |
| WO | 01/37775 A1 | | 5/2001 | |

OTHER PUBLICATIONS

IEnglish translation of the ISA Written Opinion of May 29, 2019, form PCT/ISA/237 provided by the International Bureau.
Copending continuation-in-part (C-I-P) U.S. Appl. No. 17/071,328, filed Oct. 15, 2020.

* cited by examiner

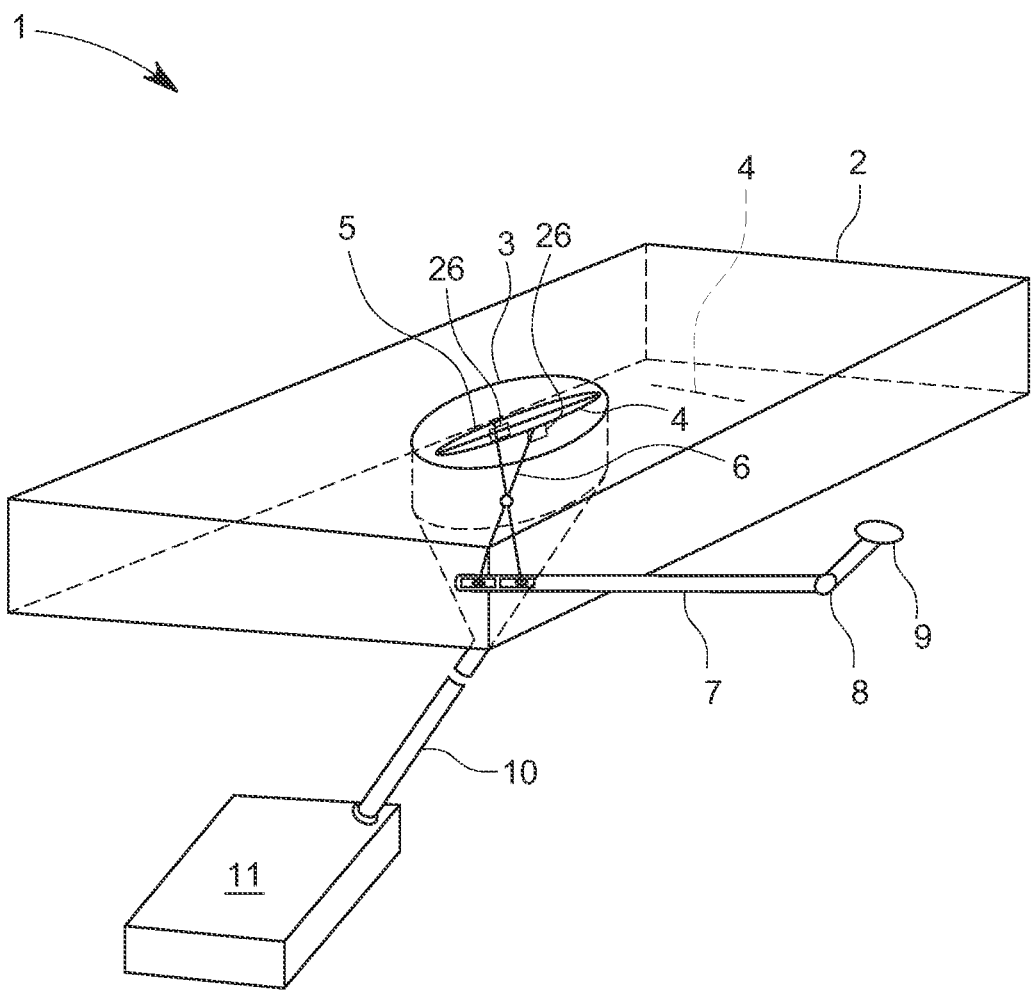

DEVICE FOR THE DISCHARGE OF URINE

CROSS-REFERENCE TO RELATED APPLICATIONS

This application is a 35 U.S.C. 371 national-phase entry of PCT International application no. PCT/CH2019/000012 filed on Apr. 11, 2019 and also claims benefit of priority to prior Swiss national application no. CH 00466/18 filed on Apr. 12, 2018, and parent PCT International application no. PCT/CH2019/000012 is integral with this present U.S. national phase entry application.

BACKGROUND

The present disclosure pertains to devices for the discharge of urine, in particular for the soiling-free discharge of urine from a person situated on a bed or a seat.

Soilings via splashing can occur during so-called standing urination, in particular as practiced by men. Hence, various urination aids such as, for example, tubular or tube-like urination aids according to DE 19916283A1 or DE 1010391064, have already been proposed that are to enable a splash-free drainage of urine, also for women, into a toilet.

In addition, even in the case of restricted mobility of the persons concerned, a urination or a defecation may be merely limited and/or may not be free of contamination. This is the case with bedridden persons in hospitals or nursing homes who are dependent on aids, such as sliders or bed pans, and on the support of third parties. This is uncomfortable for the persons concerned, and without the assistance of third parties, contamination of the bed may occur, giving rise to additional cleaning and maintenance expenditures.

SUMMARY

It is within the scope of the present disclosure therefore to create devices for discharging urine that permit hygienic urination with little effort while lying or sitting.

This object may be achieved within the scope of the present disclosure.

According to the present disclosure, a bed, in particular a bed's mattress, is provided with a slot that extends end-to-end continuously through the thickness of the mattress. An insert is arranged in the region of the slot. The slot can be expanded manually or by means of a clamping arrangement, so that the insert may be accordingly removed and inserted with little effort.

For a very low-force operation, a clamping arrangement is advantageously installed on or under the insert in the slot.

Further advantageous versions are disclosed within the scope of the present disclosure.

So, for example, the clamping arrangement may be designed in the form of a clamping frame structure, or plates that can move relative to one another.

Besides a contamination-free discharge of the urine, the device according to the invention makes possible a hygienic and odorless storage of same until disposal.

A device within the scope of the present disclosure is particularly suitable for men's urination, but may also be adapted to the physical conditions of women.

BRIEF DESCRIPTION OF THE DRAWINGS

An example is described more closely below in an exemplary embodiment with the aid of a drawing. Utilizing the example of a bed, the drawing having FIG. 1 depicts an exemplary device according to the present disclosure.

DETAILED DESCRIPTION

A normal bed 1 is equipped with a mattress 2 that, in the area of the lower abdomen, is provided with a slot 4 that may be opened and closed elastically and which extends continuously over the thickness of the mattress 2, running parallel to the longitudinal sides of the mattress 2; and which is approximately the same distance from the longitudinal sides of the mattress 2. The slot 4 preferably has a length of at least 20 cm and can be opened/widened at least 5 cm. In the FIGURE, this slot 4 is depicted simplified in closed state with side walls lying against one another.

The mattress 2 is covered with a sheet that is also cut open in the area of the slot 4, and the mattress 2 is provided with an insert 3 made of eudermic (skin-friendly), water-repellent and easily cleanable material in the region of the slot 4. The insert 3 also extends along the side walls of the slot 4 down to the bottom of the mattress 2. The insert 3 may be a part of the sheet or applied to it, or rather be introduced into the slot 4, as a separate element. In addition, the mattress 2 may have a trough depression in the direction of the slot 4.

Alternatively or in addition, the mattress 2 may also be provided with a slot that is arranged closer to a long side of the mattress 2 and that runs approximately parallel to the narrow sides of the mattress 2, as indicated in FIG. 1.

At the slot 4, there is arranged on or below the insert 3 a clamping frame structure 5 that is connected to a scissors mechanism 6 extending outside/beyond the underside of the mattress.

The clamping frame structure 5 and the scissors mechanism 6 are preferably made of a corrosion-resistant material, for example a light metal or a resilient plastic.

The clamping frame structure 5 may also be designed in the form of tongs or in some other way. Regardless of the form of structure, it must be able to widen the slot when the scissors mechanism 6 is actuated.

Likewise, instead of the scissors mechanism 6, a gear tooth segment may be employed, or a folding membrane that opens when pressure is applied may be arranged in the slot 4.

The lever ends of the scissors mechanism 6 opposite to the clamping frame structure 5 are coupled to a lever 7 (pull rod, pull cable, etc.), the other end of which is provided with a joint 8 that is in operative connection with a handle 9. Through that is rendered possible opening and closing movement of the scissors mechanism 6, or rather the clamping frame structure 5, as shown in the FIGURE. During an opening movement of the clamping frame structure 5, the material of the mattress is pushed aside at the slot 4 and an open area is formed.

Furthermore, the scissors mechanism 6, possibly including the lever 7, may also be motor operated, in which case particularly electric drives or pneumatic drives succeed in application. The scissors mechanism 6 may preferably be opened or closed by means of a left-right switching movement. The drive can, for example, be activated by means of a wire-connected sensor, wirelessly using gesture control or by means of an app.

Instead of the clamping frame structure, the clamping arrangement may also be designed in the form of plates arranged hinge-connected on one side. In closed state they lie against one another and can be opened in a V-shape by means of, for example, a rotatable rod.

In another version, the two plates 26 can also be arranged movable relative to one another and moved by means of cylinder or screw drive, but without an articulated connection to one another.

It is also possible, in a simplified embodiment, to dispense with clamping elements and rather to manually widen the slot 4 and correspondingly also to manually manipulate the insert 3.

The slot 4 descends to the underside or below the mattress 2 in liquid- and odor-tight manner into a conduit 10, for example a hose, to a tank 11 for collection of urine, and, as the case may be, feces. In order to be completely emptied, the conduit 10 is placed sufficiently sloped.

Instead of the slot, simply a permanent opening (round or oval) with an insert part (manually driven or motor driven) could be provided.

For use of the exemplary device according to the present disclosure, the person lying in bed 1 must operate the handle 9 in such a way that by means of the scissors mechanism 6 slot 4 is opened to such an extent that, for example, a penis can be placed above or therein so that the person can release his water exclusively and splash-free into slot 4.

In another version a flap (not depicted) at the connection between the line 10 and the tank 11 is opened at the same time with the actuation of the handle 9, so that all urine enters the tank 11 and no liquid remains in the line. After completion of the procedure, this flap is closed again manually or after a preset time.

The closed slot 4 intrinsically already functions as an odor trap.

For disinfection/drying of the exemplary device, in particular the clamping arrangement, UV light and/or a disinfectant spray may be introduced into the slot or the insert part. This can be carried out manually or by means of a sensor responding to the open position and/or humidity.

The person or a third party can empty and clean the tank 11 at necessary time intervals.

The device according to the present disclosure can also be arranged in a seat or in the region of a front edge of a chair or driver's seat, in fashion adapted to the seat. Thus, urinating is possible while sitting, or for drivers, during driving or in a traffic jam.

LIST OF REFERENCE LABELS

1 Bed
2 Mattress
3 insert
4 slot
5 clamping frame structure
6 scissors mechanism
7 lever
8 joint
9 handle
10 conduit
11 tank
26 plates

What is claimed is:

1. A device for discharging bodily waste, the device comprising:
    a body-supporting mattress, said mattress having a thickness, said mattress having a first, body-supporting side, said mattress having a second, lower side;
    a controllably openable and closable slot provided in said body-supporting mattress, said slot extending through the thickness of said mattress end-to-end from said first side to said second side;
    an insert, said insert being arranged in a region of said slot;
    a clamping frame structure disposed at said slot;
    a scissors mechanism, said scissors mechanism having a proximal end operatively connected to said clamping frame structure, said scissors mechanism having pivot-connected arms extending away from said second, lower side of said mattress, said pivot-connected arms extending to a mutual pivot connection situated underneath said lower side of said mattress, and said pivot-connected arms further extending away from said second, lower side of said mattress to a scissors mechanism distal end;
    a lever, said lever having a first end operatively connected to said distal end of said scissors mechanism, said lever having a second end; and,
    a joint provided at said second end of said lever, said joint being operatively connected to a handle.

2. The device for discharging bodily waste as claimed in claim 1, wherein:
    said slot is elastically openable and closable.

3. A device for discharging bodily waste as claimed in claim 1, the device further comprising:
    a conduit in operative communication with said slot, said conduit extending below said second side.

4. A device for discharging bodily waste as claimed in claim 3, the device further comprising:
    a tank connected to said conduit.

5. A device for discharging bodily waste as claimed in claim 1, the device further comprising:
    at least one lateral side of said mattress, said slot being formed to extend approximately parallel to said at least one lateral side of said mattress.

6. A device for discharging bodily waste as claimed in claim 1, the device further comprising:
    relatively movable clamping plates provided at said clamping frame structure.

7. A device for discharging bodily waste, the device comprising:
    a body-supporting mattress, said mattress having a thickness, said mattress having a first, body-supporting side, said mattress having a second, lower side;
    a controllably openable and closable slot provided in said body-supporting mattress, said slot extending through the thickness of said mattress end-to-end from said first side to said second side;
    an insert, said insert being arranged in a region of said slot;
    a clamping frame structure disposed at said slot; and,
    a scissors mechanism, said scissors mechanism having a proximal end operatively connected to said clamping frame structure to controllably open and close said slot, said scissors mechanism having pivot-connected arms extending away from said second, lower side of said mattress, said pivot-connected arms extending to a mutual pivot connection situated underneath said lower side of said mattress, and said pivot-connected arms further extending away from said second, lower side of said mattress to a scissors mechanism distal end.

8. A device for discharging bodily waste as claimed in claim 7, the device further comprising:
    an actuation lever, said lever having a first end operatively connected to said distal end of said scissors mechanism.

9. A device for discharging bodily waste as claimed in claim 8, the device further comprising:

a handle operatively connected to move said actuation lever.

10. The device for discharging bodily waste as claimed in claim 7, wherein:

said slot is elastically openable and closable.

11. A device for discharging bodily waste as claimed in claim 7, the device further comprising:

a conduit in operative communication with said slot, said conduit extending below said second side.

12. A device for discharging bodily waste as claimed in claim 11, the device further comprising:

a tank connected to said conduit.

13. A device for discharging bodily waste as claimed in claim 7, the device further comprising:

at least one lateral side of said mattress, said slot being formed to extend approximately parallel to said at least one lateral side of said mattress.

14. A device for discharging bodily waste as claimed in claim 7, the device further comprising:

relatively movable clamping plates provided at said clamping frame structure.

* * * * *